United States Patent [19]

Stamler

[11] Patent Number: 5,891,735

[45] Date of Patent: Apr. 6, 1999

[54] METHOD FOR MEASURING NITRIC OXIDE IN NITROSYL (FEII)-HEMOGLOBIN AND S-NITROSOHEMOGLOBIN

[75] Inventor: Jonathan S. Stamler, Chapel Hill, N.C.

[73] Assignee: Duke University Medical Center, Durham, N.C.

[21] Appl. No.: 616,259

[22] Filed: Mar. 15, 1996

Related U.S. Application Data

[60] Provisional application No. 60/003,801 Sep. 15, 1995.

[51] Int. Cl.⁶ .................................................. G01N 33/72
[52] U.S. Cl. ................................ 436/66; 422/52; 436/63; 436/86; 436/106; 436/107; 436/114; 436/116; 436/117; 436/118; 436/172; 436/175
[58] Field of Search .................................. 422/52; 436/63, 436/66, 86, 106, 107, 114, 116, 172, 175, 117, 118

[56] References Cited

U.S. PATENT DOCUMENTS

| | | | |
|---|---|---|---|
| 3,967,933 | 7/1976 | Etess et al. | 23/232 E |
| 3,973,910 | 8/1976 | Fine | 23/230 PC |
| 3,996,008 | 12/1976 | Fine et al. | 23/254 R |
| 4,018,562 | 4/1977 | Parks et al. | 436/114 |
| 4,066,411 | 1/1978 | Fine et al. | 23/253 PC |
| 4,193,963 | 3/1980 | Bruening et al. | 436/116 |
| 4,236,895 | 12/1980 | Stahl | 23/232 R |
| 4,301,114 | 11/1981 | Rounbehler et al. | 436/107 |
| 4,368,262 | 1/1983 | Bucovaz et al. | 435/23 |
| 4,657,744 | 4/1987 | Howard | 436/116 |
| 4,822,564 | 4/1989 | Howard | 422/52 |
| 5,094,815 | 3/1992 | Conboy et al. | 422/52 |
| 5,151,369 | 9/1992 | Lewis et al. | 436/67 |
| 5,258,311 | 11/1993 | Lewis et al. | 436/63 |
| 5,346,599 | 9/1994 | Stamler et al. | 204/180.1 |
| 5,366,900 | 11/1994 | Conboy et al. | 436/106 |
| 5,380,824 | 1/1995 | Marschall et al. | 530/385 |
| 5,459,076 | 10/1995 | Stamler et al. | 436/116 |

FOREIGN PATENT DOCUMENTS

WO 93/21525  10/1993  WIPO.

OTHER PUBLICATIONS

Stamler, Jonathan S., et al., "Nitric Oxide Circulates in Mammalian Plasma Primarily as an S–Nitroso Adduct of Serum Albumin," *Proc. Natl. Acad. Sci. USA*, 89:7674–7677 (1992).

Gaston, Benjamin, et al., "Endogenous Nitrogen Oxides and Bronchodilator S–Nitrosothiols in Human Airways," *Proc. Natl. Acad. Sci. USA*, 90:10957–10961 (1993).

Sonoda, Masaru et al., "Diazotization Reaction of Nitric Oxide Trapped by Hemoglobin," *Life Sciences*, 55(11):199–204 (1994).

Murphy, M.E. and Noack, E., "Nitric Oxide Assay Using Hemoglobin Method," *Methods in Enzymology*, 233:240–249 (1994).

Stamler, J.S. and Feelisch, M., "Preparation and Detection of S–Nitrosothiols," *Methods in Nitric Oxide Research*, M. Feelisch and J.S. Stamler, eds., John Wiley & Sons, Ltd. (1996).

Saville, B., "A Scheme for the Colorimetric Determination of Microgram Amounts of Thiols," *Analyst* 83:670–672 (1958).

*Primary Examiner*—Lyle A. Alexander
*Assistant Examiner*—S. Carrillo
*Attorney, Agent, or Firm*—Hamilton, Brook, Smith & Reynolds, P.C.

[57] ABSTRACT

Nitrosyl (FeII) hemoglobin can be detected in biological samples, using a method which involves injections of samples into a photolysis cell, prior to detection of chemiluminescence generated by the reaction between nitric oxide and ozone. This method is useful for monitoring the levels of nitric oxide bioactivity in both normal physiological states, and disease states, such as septic shock, atherosclerosis, thrombosis, hyperhomocysteinemia, pulmonary hypertension, malignancy, infections and central nervous system disorders.

18 Claims, No Drawings

METHOD FOR MEASURING NITRIC OXIDE IN NITROSYL (FEII)-HEMOGLOBIN AND S-NITROSOHEMOGLOBIN

RELATED APPLICATIONS

This application claims priority to U.S. Provisional Application Number 60/003,801 filed on Sept. 15, 1995.

BACKGROUND OF THE INVENTION

Endothelium-derived relaxing factor (EDRF), is a product of the normal endothelial cell, and has both vasodilatory and antiplatelet properties (Furchgott, R. F. et al., *Nature*, 288:373–376 (1980); Moncada, S. et al., *Biochem. Pharmacol*, 38:1709–1713 (1989); Azuma, H. et al., *Brit. J. Pharmacol.* 88:411–415 (1986) and Radomski, M. W. et al., *Brit. J. Pharmacol.* 92:639–642 (1987)). Pharmacologic studies suggest that disease states as varied as septic shock, hyper-homocysteinemia, atherosclerosis, and hypoxia-induced pulmonary hypertension may be associated with abnormal concentrations of EDRF in the vascular milieu (Westernberger, U. et al., *Free Rad. Res. Comm.* 11:167–168 (1990); Yamamoto, H. et al., *J. Clin. Invest.* 81:1752–1758 (1988); Dinh-Xuan, A. T. et al., *Engl. J. Med.* 324:1539–1547 (1991)). This bioactive substance is believed to be equivalent to nitric oxide, or a chemical congener or adduct thereof (Palmer, R. M. G. et al., *Nature* 327:524–525 (1987); Ignarro, L. J. et al., *Proc. Natl. Acad. Sci.* 84:9265–9269 (1987)). Among the species of importance as biological adducts of nitric oxide are S-nitrosothiols, which are adducts with the sulfhydryl groups of amino acids, peptides, and proteins.

It has been demonstrated that nitric oxide and authentic EDRF react with free thiol groups of proteins under physiologic conditions in vitro, to form S-nitroso-proteins. These nitric oxide adducts have bioactivities which are comparable to nitric oxide, but exhibit half-lives on the order of hours, significantly longer than that of EDRF (Stamler, J. S. et al., *Proc. Natl. Acad. Sci.* 89:444–448 (1992)).

Under normal circumstances, the concentration of nitric oxide in blood or plasma is believed to be quite low (in the 1 nM range) and its half-life of the order of 0.1 second. Its high degree of reactivity toward oxygen and redox metals, in conjunction with its extremely short half-life, have made the routine measurement of blood levels in both normal and disease states most difficult by standard methods, such as chemiluminescence spectroscopy, electron paramagnetic resonance spectroscopy, or differential absorbance spectroscopy of hemoglobin (Martin, W. et al., *J. Pharmacol. Exp. Therap.* 237:529–538 (1986); Downes, M. J. et al., *Analyst* 101:742–748 (1976); Kelm, M. et al., *Circ. Res.* 66:1561–1575 (1990); Arroyo, C. M. et al., *Free Rad. Res. Comm.* 14:145–155 (1991) and Goretsky, J. et al., *J. Biol. Chem.* 263:2316–2323 (1988)). In fact, it is generally assumed in the field that such measurements are not feasible by currently used methods.

Nitrosonium ($NO^+$) is a short lived species which is too unstable to exist freely in biological systems, and felt to be non-detectable by chemiluminescence. Nitric oxide exists in the S-nitrosothiol adduct, not as nitric oxide but rather as a nitrosonium equivalent. Thus, it behaves chemically in a manner which more closely resembles $NO_+$ than $NO^-$ (nitric oxide).

Hemoglobin (Hb) is a tetramer comprised of two alpha and two beta subunits. In human Hb, each subunit contains one heme, while the beta ($\beta$) subunits also contain highly reactive thiol (SH) groups (cys$\beta$93) (Olson, J. S., *Meth. of Enzym.*, 76:631–651 (1981; Antonini & Brunori, *In Hemoglobin and Myoglobin in Their Reactions with Ligands*, American Elsevier Publishing Co., Inc., New York, pp.29–31 (1971)). These cysteine residues are highly conserved among species. Nitric oxide (NO) interacts with hemoglobin at its metal centers, whereas S-nitrosothiols (RSNOs) can donate the NO group to $\beta$93 cysteine residues.

Nitric oxide is known to bind tightly to hemoglobin, forming nitrosyl(FeII)-hemoglobin. Interactions of NO with ahemoglobin are believed to be a major route of NO metabolism in biological systems. It follows that levels of NO-hemoglobin in blood should be an excellent indication of endogenous NO production. However, methods have not been developed that are sufficiently sensitive to make this determination in vivo (Beckman, J. S. et al., *Methods in Nitric Oxide Research*, Feelisch and Stainler, J. S. eds, Wiley, Chichester, U.K. (1996)). Specifically, electron paramagnetic resonance (EPR) has been used previously to measure nitric oxide bound to the Fe of the heme. However, under normal physiological conditions, circulating levels of NO-hemoglobin in blood are below the detection limit. The insensitivity of EPR makes this method impossible to use to monitor all but a gross change in NO-hemoglobin from normal levels. Only in pathophysiological states such as sepsis and pregnancy, which are characterized by NO overproduction, can EPR be used to detect a measurable level for NO in blood.

EPR measurements also suffer from being cumbersome and expensive. An alternative method of measuring NO by assaying nitrite/nitrate in body fluids also suffers from insensitivity.

SUMMARY OF THE INVENTION

The invention is a method for measuring nitrosyl(FeII)-hemoglobin in blood using a series of steps in which a protein fraction is prepared from blood cells and the protein fraction is assayed for the formation of nitric oxide by photolysis of the protein fraction followed by measuring a chemiluminescence signal generated by a chemical reaction between nitric oxide and ozone. cl DETAILED DESCRIPTION The invention relates to a method for determining the concentration of nitrosyl(FeII)-hemoglobin in a blood sample, thereby serving as a measure of the level of NO in the animal or human from which the blood sample has been taken. The method is related to one used previously for the measurement of S-nitrosoproteins and smaller molecular weight S-nitrosothiols in plasma (See U.S- Ser. No. 5,459, 076; Oct. 17, 1995. The contents of this patent are hereby incorporated by reference in their entirety.) However, the primary focus of the present invention is on assaying for nitrosyl(FeII)-hemoglobin rather than S-nitrosothiols.

In contrast to the previous method, in which the red blood cells were removed and discarded from the sample to be analyzed, the subject invention method uses the red blood cells. The method measures NO which has reacted with the thiol groups of hemoglobin in the form of S-nitroso-hemoglobin (SNO-Hb) as well as NO bound to the Fe of the heme (nitrosyl(FeII)-hemoglobin or Hb(FeII)NO). As shown in the table, the level of S-nitroso-hemoglobin in venous blood is negligible compared to the level of Hb(FeII) NO. Therefore, to specifically measure the level of Hb(FeII) NO in venous blood, it is unnecessary to include steps in which Hb samples are divided into two aliquots which are then either treated or not treated with a 10-fold excess of $HgCl_2$ over the protein concentration. Reaction of Hb with $HgCl_2$ removes NO from thiol groups selectively, without disturbing NO bound at the heme. Values for NO obtained from the $HgCl_2$ reaction, if significant, should be subtracted from the total NO obtained for the measurements without the $HgCl_2$ reaction, to obtain an accurate value for Hb(FeII) NO.

In one embodiment of the invention, a blood sample is taken from a mammal, such as a human, and the solid parts including cells are isolated away from the remaining fluid. The cells are then lysed by standard methods, and a protein fraction is prepared. Before quantitating nitric oxide adducts (nitrosonium adducts, which include low molecular weight S-nitrosothiols such as S-nitrosoglutathione and high molecular weight S-nitrosothiols such as S-nitrosoproteins), it is preferable to first remove low molecular weight S-nitrosothiols endogenous to the red blood cells, which would also contribute to the NO value, by a step which separates low molecular weight molecules away from the red blood cell proteins (referred to as desalting). This step can include, for example, dialysis or column chromatography based on separation by size of the molecules. A further step is to subject the protein fraction to photolysis, as in a photolysis cell, where it is irradiated with light of the appropriate wavelength to liberate NO from the various forms of hemoglobin. The resulting NO is detected by reaction with ozone.

One embodiment of the invention utilizes a chemiluminescence apparatus in which a photolysis cell is linked directly to the reaction chamber and detector portion, thereby bypassing the pyrolyzer. A sample of the blood protein fraction is injected into the photolysis cell, either directly, or as chromatographic effluent from a high-performance liquid or gas chromatography system which is connected to the photolysis cell.

The sample is then irradiated with a mercury vapor lamp, and directed through a series of cold traps, where liquid and gaseous fractions which are less volatile than nitric oxide (such as nitrite and nitrate) are eliminated, leaving only free nitric oxide remaining in the cell. The nitric oxide is then transported by a gaseous stream, preferably helium, into the chemiluminescence spectrometer. In the alternative, other inert gases may be used.

Once present in the chemiluminescence spectrometer, the free nitric oxide is detected by its chemical reaction with ozone, resulting in the generation of signals that are recorded on a digital integrator. If desired, flow rates and illumination levels in the photolysis cell can be adjusted to cause complete photolysis of the S-nitric oxide bond of the S-nitrosothiol compounds. Flow rates and illumination levels may be adjusted by routine methods available in the art, in order to achieve optimal cleavage of the bond between the particular adduct and nitric oxide, nitrosonium or nitroxyl, whichever is bound.

In a variation, the invention relates to a method for detecting S-nitrosothiols, including primarily S-nitrosohemoglobin (SNO-Hb) in a blood sample. This method comprises inactivating the chemiluminescence, signal-generating capability of any nitric oxide which is associated with a thiol, in the protein fraction derived from the blood sample, and determining the amount of thiol-bound nitric oxide by measuring the quantitative difference between total nitric oxide and nitric oxide remaining after inactivation.

A particular embodiment of this variation relates to a method in which the protein fraction derived from the blood sample is treated with a source of mercurous ion, followed by air incubation, which oxidizes the nitric oxide and nitrosonium and renders them undetectable. Compounds suitable for pretreatment include $Hg_2Cl_2$ and other mercurous ion salts and organic mercurials. The treated sample is then injected into the photolysis cell, where $NO^+$ is converted to $NO^-$ (nitric oxide) and the nitric oxide is detected by the chemiluminescence method described above. The amount of nitric oxide which is specifically derived from S-nitrosothiols is determined by comparing the chemiluminescence signal generated by the mercurous ion-treated sample, with a chemiluminescence signal generated by a sample of the equivalent biological fluid which is not treated with mercurous ion prior to injection into the photolysis cell.

In a further embodiment of the claimed invention, the methods described herein may be utilized to determine the presence of a disease state which involves abnormal levels of nitric oxide and its biologically active equivalents, by monitoring Hb(FeII)NO and SNO-Hb levels in blood, and more particularly, Hb(FeII)NO in venous blood from a patient. The ability to specifically assay for Hb(FeII)NO in venous blood distinguishes this assay over previously known methods. Nitric oxide adducts represent a pool of bioactive nitric oxide in physiological systems. Therefore, in disease states in which the pathogenesis derives from the effects of abnormal levels of nitric oxide, these methods provide a means for the clinician to determine the presence of, and monitor the extent of, the disease state. Such information enables the clinician to determine the appropriate pharmacological intervention necessary to treat the disease state. Such disease states and medical disorders include, but are not limited to, septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infections, inflammation, asthma, tolerance to narcotics and central nervous system disorders. Furthermore, the use of these methods is not limited to these diseases. This method can be of use in assaying biologically active nitric oxide equivalents in any disease state or medical disorder in which nitric oxide is implicated.

EXAMPLES

Example 1
Methods and Control Experiments

Initially, to modify the chemiluminescence apparatus for use in the detection method, a photolysis cell, consisting of a borosilicate glass coil (3 m×0.64 cm o.d.×1 mm i.d., turned to a diameter of 6 cm and a width of 12 cm), with a purge stream of helium (5 L/min), was linked directly to the reaction chamber and detector portion of a chemiluminescence apparatus (Model 543 Thermal Energy Analyzer, Termedix, Inc., Woburn, Mass.), thereby bypassing the pyrolyzer. Then, a 5–100 μl volume sample was either introduced directly, or as a chromatographic effluent from an attached high-performance liquid or gas chromatography system into the photolysis cell, and irradiated with a 200-watt mercury vapor lamp (vertically mounted in the center of the photolysis coil on TEFLON towers). The effluent from the photolysis coil was directed to a series of cold traps where liquid and gaseous fractions less volatile than nitric oxide (such as nitrite and nitrate), were removed.

The nitric oxide was then transported by a helium stream into the chemiluminescence spectrometer, in which free nitric oxide was detected by reaction with ozone. Signals were recorded on a digital integrator (Model 3393A, Hewlett Packard, Andover, Mass., USA). Flow rates and illumination levels in the photolysis cell were designed to result in complete photolysis of the S-nitric oxide bond, as confirmed by analysis of effluent from the photolysis cell, according to standard methods (Saville, B., *Analyst* 83:670–672 (1958)).

To determine the fraction of nitric oxide which was derived from S-nitrosothiols, several additional steps were included in the method described above. Prior to its injection into the photolysis cell, an aliquot of the same sample was treated with an 8 to 10-fold excess of Hg over protein concentration followed by air incubation, according to standard methods (Saville, B., *Analyst* 83:670–672 (1958)), in order to oxidize the nitric oxide displaced as nitrosonium and render it undetectable. Nitric oxide concentrations from samples alternatively subjected to or not subjected to, pretreatment with $HgCl_2$, were compared, to determine how much of the nitric oxide detected was derived specifically from S-nitrosothiols. Similarly, as an added measure of confirmation, S-nitrosothiols and free nitric oxide were compared using nitric oxide concentrations in samples alternatively exposed to, or not exposed to, photolysing illumination.

S-nitroso-L-cysteine, S-nitroso-glutathione, S-nitroso-N-acetyl-L-cysteine and S-nitroso-bovine serum albumin were synthesized by exposing the respective thiols to acidified $NaNO_2$, according to routine methods, and standard curves were generated (Stamler, J. S. et al., *Proc. Natl. Acad. Sci.* 89:444–448 (1992)). Similarly, standard curves were derived for nitric oxide generated from acidified $NaNO_2$, or from a saturated solution of nitric oxide gas serially diluted immediately before measurement in airtight syringes. Concentration-response curves were linear with correlation coefficients of $\geq 0.98$ in all cases. Limits of sensitivity were approximately 0.1 pM, and intraassay variability was ±3%.

The response of this system to pure S-nitrosothiols was first examined using S-nitroso-L-cysteine as a standard. The concentration of the stock solution from which serial dilutions were made was determined by standard methods and confirmed by the optical density at 340 nm (Saville, B., *Analyst* 83:670–672 (1958); and Stamler, J. S. et al., *Proc. Natl. Acad. Sci.* 89:444–448 (1992)). Serial dilutions were prepared with concentrations ranging from 100 µM to 0.1 pM. The chemiluminescence signal was linear over this concentration range (correlation coefficient of $\geq 0.98$).

As additional controls, S-nitroso-glutathione, and S-nitroso-N-acetyl-L-cysteine were also synthesized and responses measured. In the absence of photolysis, the nitric oxide signal was below the limits of detectability. Similarly, $HgCl_2$ pretreatment of the samples, followed by incubation in air to oxidize (and render undetectable) the liberated nitric oxide led to a loss of >99% of the chemiluminescence signal in all cases.

Example 2
Endogenous Levels of S-nitrosohemoglobin and Nitrosyl (FeII)-Hemoglobin in Blood To determine if SNO-Hb is naturally occuring in the blood, and if so, its relationship to the $O_2$ transport capacity and nitrosylated-heme content of red cells, we developed an analytical approach to assay the S-nitrosothiol and nitrosyl-heme content of erythrocytes. Arterial blood was obtained from the left ventricle of anesthetized rats by direct puncture and venous blood was obtained from the jugular vein and inferior vena cava. Hb was then purified from red cells and assayed for RSNO and (FeII)NO content. Arterial blood contained significant levels of SNO-Hb, whereas levels were virtually undetectable in venous blood. (See table.) Measurements made 45 minutes after infusion of the NO synthase inhibitor $N^\omega$-monomethyl-L-arginine (L-NMMA) (50 mg/kg), showed a depletion of SNO-Hb as well as total Hb-NO (82 and 50±18%, respectively; n=3–5; p<0.05). These data establish the endogenous origin of SNO-Hb, although some environmental contribution is not excluded. The arterial-venous distribution seen for SNO-Hb was reversed in the case of Hb(FeII)NO, which was detected in higher concentrations in partially deoxygenated (venous) erythrocytes. Accordingly, the proportion of nitrosylated protein thiol and heme appears to depend on the oxygenation state of the blood. Consistent with these findings, Wennmalm and coworkers have shown that Hb(FeII)NO forms mainly in venous (partially deoxygenated) blood (Wennmalm, A., et al., Br. *J. Pharmacol.*, 106(3):507–508 (1992)). However, levels of Hb(FeII)NO in vivo are typically too low to be detected (by EPR) and SNO-Hb is EPR-silent (i.e. it is not paramagnetic). Thus, photolysis-chemiluminesence represents an important technological advance, as it is the first methodology capable of making quantitative and functional assessments of NO binding to Hb under normal physiological conditions.

Blood was obtained from the left ventricle (arterial) and jugular vein (venous) of anesthetized Sprague-Dawley rats. Comparable venous values were obtained in blood from the inferior vena cava. Red blood cells were isolated by centrifugation at 800 g, washed three times in phosphate buffered saline at 4° C., lysed by the addition of 4-fold excess volume of deionized water containing 0.5 mM EDTA, and desalted rapidly across G-25 columns according to the method of Penefsky at 4° C. In 24 rats, Hb samples were divided in two aliquots which were then treated or not treated with 10-fold excess $HgCl_2$ over protein concentration as measured by the method of Bradford. Determinations of SNO-Hb and Hb(FeII)NO were made by photolysis-chemiluminescence as described below. In 12 additional rats, further verification of the presence of SNO-Hb was made by assaying for nitrite after $HgCl_2$ treatment. Specifically, samples (with and without $HgCl_2$) were separated across Amicon-3 (Centricon filters, m.w. cut off 3,000) at 40° C. for 1 h, and the low molecular weight fractions collected in airtight syringes containing 1 µM glutathione in 0.5N HCl. Under these conditions, any nitrite present was converted to S-nitrosoglutathione, which was then measured by photolysis-chemiluminescence (detection limit ~1 nM). SNO-Hb was present in all arterial samples, and levels determined by this method (286 ± ±33 nM) were virtually identical to and not statistically different from those shown in the table. In venous blood, SNO-Hb was undetectable (0.00±25 nM); levels were not statistically different from those given above.

Method of Assay on Rat Blood

As a part of the assay, a highly sensitive photolysis-chemiluminescence methodology was employed, which had been used for measuring RSNOs (S-nitrosothiols) in biological systems (Gaston, B., et al., (1993); Stamler, J. S., et al., (1992)). The method involves photolytic liberation of NO from the thiol, which is then detected in a chemiluminesence spectrometer by reaction with ozone. The same principle of operation can be used to cleave (and measure) NO from nitrosyl-metal compounds (Antonini, E. Brunori, M. *In Hemoglobin and Myoglobin in Their Reactions with Ligands*, American Elsevier Publishing Co., Inc., New York, pp. 29–31 (1971)). With adjustment of flow rates in the photolysis cell, complete photolysis of the NO ligand of Hb(FeII)NO could be achieved. Standard curves derived from synthetic preparations of SNO-Hb, Hb(FeII)NO, and S-nitrosoglutathione were linear (R>0.99), virtually. superimposable, and revealing of sensitivity limits of approximately 1 nM. Two analytical criteria were then found to reliably distinguish SNO-Hb from Hb(FeII)NO: 1) signals from SNO-Hb were eliminated by pretreatment of samples with 10-fold excess $HgCl_2$, while Hb(FeII)NO was resistant to mercury challenge; and 2) treatment of SNO-Hb with $HgCl_2$ produced nitrite (by standard Griess reactions) in quantitative yields, whereas similar treatment of Hb(FeII) NO did not. UV/VIS spectroscopy confirmed that NO remained attached to heme in the presence of excess $HgCl_2$.

TABLE

Endogenous levels of S-nitrosohemoglobin and nitrosyl(FeII)-hemoglobin in blood

| Site | SNO-Hb (nM) | Hb(FeII) NO (nM) |
| --- | --- | --- |
| Arterial | 311 ± 55* | 536 ± 99† |
| Venous | 32 ± 14 | 894 ± 126 |

*P < 0.05 vs venous;
†P < 0.05 for paired samples vs venous

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method for measuring nitric oxide equivalents in S-nitrosohemoglobin and nitrosyl(FeII)-hemoglobin a blood sample comprising red blood cells, said method comprising the steps of:
   a) lysing the red blood cells of said blood sample containing said S-nitrosohemoglobin and said nitrosyl (FeII)-hiemioglobin;
   b) preparinig a desalted protein fraction from said lysed red blood cells;
   c) subjecting the desalted protein fraction to photolysis, thereby liberating nitric oxide from S-nitrosohemoglobin and nitrosyl(FeII)-hemoglobin;
   d) generating a chemiluminescent reaction between said liberated nitric oxide and ozone; and
   e) quantitating the liberated nitric oxide in the desalted protein fraction by measuring a chemiluminescence signal generated by said reaction between said nitric oxide and said ozone, thereby measuring nitric oxide equivalents in S-nitrosohemoglobin and nitrosyl(FeII)-hemoglobin in said blood sample.

2. A method for measuring nitric oxide bound to Fe in nitrosyl(FeII)-hemoglobin in a sample of venous blood comprising red blood calls, said method comprising the steps of:
   a) lysing the red blood cells in said sample of venous blood containing said nitrosyl(FeII)-hemoglobin, thereby obtaining lysed red blood cells;
   b) isolating a desalted protein fraction from the lysed red blood cells;
   c) subjecting the desalted protein fraction to photolysis, thereby liberating nitric oxide from nitrosyl(FeII)-hemoglobin;
   d) generating a chemiluminescent reaction between said liberated nitric oxide and ozone; and
   e) quantitating the liberated nitric oxide in the desalted protein fraction by measuring a chemiluminescence signal generated by said reaction between said liberated nitric oxide and said ozone, thereby measuring said nitric oxide bound to Fe in nitrosyl(FeII)-hemoglobin in said sample of venous blood.

3. A The method of claim 2, wherein the sample of venous blood is human blood.

4. A method for assaying thiol-bound NO (nitric oxides) in S-nitrosohemoglobin in a sample of purified hemoglobin, said method comprising:
   a) dividing the sample of purified hemoglobin containing said S-nitrosohemoglobin into a first aliquot and a second aliquot;
   b) contacting said first aliquot with mercury ions in excess over protein concentration in the purified hemoglobin, thereby obtaining a mercury-treated aliquot;
   c) subjecting said mercury-treated aliquot and said second aliquot to photolysis to liberate NO from said aliquots;
   d) reacting said NO from said mercury-treated aliquot and said NO from said second aliquot with ozone, thereby generating chemiluminescent signals;
   e) measuring said chemiluminescent signals; and
   f) determining a quantity of thiol-bound NO in said S-nitrosohemoglobin from a difference in measurements between NO from said mercury-treated aliquot and NO from said second aliquot.

5. The method of claim 4 wherein the mercury ions are mercuric ions.

6. A method for assaying thiol-bound nitric oxide in S-nitrosohemoglobin in a blood sample, said method comprising:
   a) isolating washed red blood cells from said blood sample containing said S-nitrosohemoglobin;
   b) lysing said red blood cells, thereby obtaining a lysate;
   c) desalting the lysate;
   d) separating the lysate into a first aliquot and a second aliquot;
   e) contacting said first aliquot of said lysate with mercury ions to obtain a mercury-treated aliquot;
   f) subjecting said mercury-treated aliquot and said second aliquot to photolysis to liberate nitric oxide from said aliquots;
   g) reacting said nitric oxide from said mercury-treated aliquot and nitric oxide from said second aliquot with ozone, thereby generating chemiluminescent signals;
   h) measuring said chemiluminescent signals; and
   i) determining a quantity of thiol-bound nitric oxide in said S-nitrosohemoglobin from a difference in measurements between nitric oxide from said mercury-treated aliquot and nitric oxide from said second aliquot.

7. The method of claim 6 wherein the mercury ions are mercuric ions.

8. A method for assaying thiol-bound NO (nitric oxide) in S-nitrosohemoglobin in a sample of purified hemoglobin, comprising the steps of:
   a) dividing the sample of purified hemoglobin containing said S-nitrosohmoglobin into a first aliquot and a second aliquot;
   b) contacting said first aliquot with mercury ions in excess over protein concentration, in the purified hemoglobin to obtain a mercury-treated aliquot;
   c) isolating from said mercury-treated aliquot a mercury-treated low molecular weight fraction, and from said second aliquot a second low molecular weight fraction;

d) contacting said mercury-treated low molecular weight fraction with excess thiol under acidic conditions and contacting said second low molecular weight fraction with excess thiol under acidic conditions, thereby producing S-nitrosothiol in said mercury-treated low molecular weight fraction and in said second low molecular weight fraction;

e) subjecting said mercury treated low molecular weight fraction and said second low molecular weight fraction to photolysis thereby liberating nitric oxide from said S-nitrosothiol in said low molecular weight fractions;

f) reacting said liberated nitric oxide in said mercury-treated low molecular weight fraction and in said second low molecular weight fraction with ozone, thereby generating chemiluminescent signals;

g) measuring said chemiluminescent signals, thereby obtaining a measurement of thiol-bound nitric oxide in said mercury-treated low molecular weight fraction and a measurement of thiol-bound NO in said second low molecular weight fraction; and h) determining said thiol-bound nitric oxide in S-nitrosohemoglobin in said sample of purified hemoglobin from a difference between said measurement of said thiol-bound nitric oxide in said mercury-treated low molecular weight fraction and said measurement of said thiol-bound nitric oxide in said second low molecular weight fraction.

9. The method of claim 8 wherein the thiol is glutathione.

10. The method of claim 8 wherein the mercury ions are mercuric ions.

11. A method for measuring NO (nitric oxide) equivalents in S-nitrosohemoglobin and nitrosyl(FeII)-hemoglobin in a blood sample comprising red blood cells, said method comprising:

a) isolating washed red blood cells from said blood sample containing said S-nitrosohemoglobin and said nitrosyl(FeII)-hemoglobin;

b) lysing the red blood cells, thereby obtaining a lysate;

c) desalting the lysate;

d) subjecting said lysate to photolysis to liberate NO from said S-niitrosohemoglobin and said nitrosyl(FeII)-hemoglobin in said lysate;

e) reacting said liberated NO with ozone, thereby generating chemiluminescence signals; and f) measuring said chemiluminescent signals, thereby measuring NO equivalents in S-nitrosohemoglobin and nitrosyl(FeII)-hemoglobin in said blood sample.

12. A method for measuring NO (nitric oxide) equivalents in nitrosyl(FeII)-hemoglobin in a sample of venous blood, said method comprising:

a) isolating washed red blood cells from said sample of venous blood containing said nitrosyl(FeII)-hemoglobin;

b) lysing the red blood cells, thereby obtaining a lysate;

c) desalting the lysate;

d) subjecting said lysate to photolysis to liberate NO from said nitrosyl(FeII)-hemoglobin in said lysate;

e) reacting said NO with ozone, thereby generating a chemiluminescent signal; and f) measuring said chemiluminescent signal, thereby measuring NO equivalents in nitrosyl(FeII)-hemoglobin in said sample of venous blood.

13. A method for measuring NO (nitric oxide) bound to nitrosyl(FeII)-hemoglobin in a sample of red blood cells, said method conspiring:

a) preparing a protein fraction from said sample of red blood cells containing said nitrosyl(FeII)-hemoglobin;

b) treating the protein fraction with excess mercury ions;

c) subjecting the protein fraction to photolysis to liberate NO from said nitrosyl(FeII)-hemoglobin;

d) reacting said liberated NO in said protein fraction with ozone, thereby generating a chemiluminescent signal; and e) measuring the chemiluminescent signal, thereby measuring NO bound to nitrosyl(FeII)-hemoglobin in said sample of red blood cells.

14. A method for measuring NO (nitric oxide) bound to Nitrosyl(FeII)-hemoglobin in a sample of purified hemoglobin, comprising treating the sample of purified hemoglobin containing said nitrosyl(FeII)-hemoglobin with excess mercury ions, subjecting the purified, treated hemoglobin to photolysis to liberate NO from said nitrosyl(FeII)-hemoglobin, reacting the NO with ozone, thereby generating a chemiluminescent signal, and measuring the chemiluminescent signal, thereby measuring NO bound to nitrosyl (FeII)-hemoglobin in said sample of purified hemoglobin.

15. A method for assaying thiol-bound nitric oxide in S-nitrosohemoglobin in a blood sample comprising red blood cells, said method comprising:

a) isolating washed red blood cells from said blood sample containing said S-nitrosohemoglobin;

b) lysing the red blood cells, thereby obtaining a lysate;

c) desalting the lysate;

d) separating the lysate into a first aliquot and a second aliquot;

e) contacting said first aliquot of said lysate with mercury ions to obtain a mercury-treated aliquot;

f) isolating from said mercury-treated aliquot a mercury-treated low molecular weight fraction, and from said second aliquot a second low molecular weight fraction;

g) contacting said mercury-treated low molecular weight fraction with excess thiol under acidic conditions and contacting said second low molecular weight fraction with excess thiol under acidic conditions, thereby producing S-nitrosothiol in said mercury-treated low molecular weight fraction and in said second low molecular weight fraction;

h) subjecting said mercury-treated low molecular weight fraction and said second low molecular weight fraction to photolysis, thereby liberating nitric oxide from said S-nitrosothiol;

i) reacting said liberated nitric oxide in said mercury-treated low molecular weight fraction and in said second low molecular weight fraction with ozone, thereby generating chemiluminescent signals;

j) measuring said chemiluminescent signals, thereby obtaining a measurement of thiol-bound nitric oxide in said mercury-treated low molecular weight fraction and a measurment of thiol-bound nitric oxide in said second low molecular weight fraction; and k) determining said thiol-bound nitric oxide in said S-nitrosohemoglobin from a difference between said measurement of said thiol-bound nitric oxide in said mercury-treated low molecular weight fraction and said measurement of said thiol-bound nitric oxide in said second low molecular weight fraction.

16. The method of claim 15 wherein the thiol is glutathione.

17. The method of claim 15 wherein the mercury ions are mercuric ions.

18. A method for assaying NO equivalents in S-nitrosohemoglobin and nitrosyl(FeII)-hemoglobin in a sample of purified hemoglobin, said method comprising:

a) subjecting said sample of purified hemoglobin containing said S-nitrosohemoglobin and said nitrosyl(FeII)-hemoglobin to photolysis, thereby liberating NO from said S-nitrosohemoglobin and said nitrosyl(FeII)-hemoglobin;

b) reacting said liberated NO with ozone, thereby generating chemiluminescent signals; and c) measuring said chemiluminescent signal, thereby measuring NO equivalents in S-nitrosohemoglobin and nitrosyl(FeII)-hemoglobin in said sample of purified hemoglobin.

* * * * *

UNITED STATES PATENT AND TRADEMARK OFFICE
CERTIFICATE OF CORRECTION

PATENT NO.   : 5,891,735
DATED        : April 6, 1999
INVENTOR(S)  : Jonathan S. Stamler It is certified that error appears in the above-identified patent and that said Letters Patent is hereby corrected as shown below:

In Column 1, after the Related Applications section, please insert the following:

--GOVERNMENT SUPPORT

This invention was made with Government support under Grant No. NIH R01 HL52529 awarded by the National Institutes of Health. The Government has certain rights in the invention.--

Signed and Sealed this

Twenty-first Day of September, 1999

*Attest:*

Q. TODD DICKINSON

*Attesting Officer*  *Acting Commissioner of Patents and Trademarks*